United States Patent
Phalin

Patent Number: 5,576,492
Date of Patent: Nov. 19, 1996

[54] MECHANICAL CONTOUR FOLLOWER

[75] Inventor: Mark C. Phalin, Enfield, Conn.

[73] Assignee: United Technologies Corporation, Hartford, Conn.

[21] Appl. No.: 378,702

[22] Filed: Jan. 26, 1995

[51] Int. Cl.$^6$ .......................... G01N 29/26; G01N 29/24
[52] U.S. Cl. ................... 73/634; 73/618; 73/629; 73/640
[58] Field of Search .............................. 73/632, 633, 634, 73/640, 618, 629, 620, 622, 627, 619

[56] References Cited

U.S. PATENT DOCUMENTS

| | | | |
|---|---|---|---|
| 3,575,043 | 4/1971 | Allen et al. | 73/67.8 |
| 3,824,843 | 7/1974 | Gebeshuber et al. | 73/71.5 |
| 4,166,395 | 9/1979 | Dannehl | 73/634 |
| 4,246,794 | 1/1981 | Sheets et al. | 73/637 |
| 4,304,133 | 12/1981 | Feamster, III | 73/633 |
| 4,472,975 | 9/1984 | Beck et al. | 73/644 |
| 4,586,379 | 5/1986 | Burkhardt, Jr. | 73/622 |
| 4,612,808 | 9/1986 | McKirdy et al. | 73/622 |
| 4,641,532 | 2/1987 | Rohrer | 73/637 |
| 4,768,155 | 8/1988 | Takishita et al. | 73/634 |
| 4,953,405 | 9/1990 | Hara et al. | 73/620 |
| 5,001,674 | 3/1991 | Kawasaki | 367/13 |

Primary Examiner—Hezron E. Williams
Assistant Examiner—Rose M. Finley
Attorney, Agent, or Firm—Malcolm J. Chisholm, Jr.

[57] ABSTRACT

A mechanical contour follower is disclosed for maintaining a transducer ninety degrees to a workpiece surface, with respect to longitudinal and transverse axes of the workpiece surface, and for keeping the transducer at a constant distance from the workpiece surface during an ultrasound inspection of the workpiece (these conditions being referred to as keeping the transducer normal to the workpiece surface). In a particular embodiment, the mechanical contour follower comprises a plunger post slideably secured to a bridge assembly of an ultrasound inspection apparatus; a support frame affixed to the plunger post, having opposed first and second pivot arms; a gimballed mounting means, having an outer ring pivotally secured to opposed pivot ends of the first and second pivot arms, and having an inner disk pivotally secured within the outer ring to produce a gimbal effect; a transducer barrel affixed to a support surface of the inner disk; and a tracking surface of the inner disk opposed to the support surface of the inner disk. The gimbal effect allows a transducer secured within the transducer barrel to remain at ninety degrees to the workpiece surface with respect to the longitudinal and transverse axes of the workpiece surface, and the slidable plunger post enables the transducer to float in a vertical axis, and thereby remain a constant distance from the workpiece surface, so that the transducer automatically remains normal to the workpiece surface throughout an inspection of the workpiece.

6 Claims, 7 Drawing Sheets

MECHANICAL CONTOUR FOLLOWER

TECHNICAL FIELD

The present invention relates to non-destructive testing of articles of manufacture, and especially relates to immersion ultrasonic inspection of articles manufactured of composite materials such as propeller blades.

BACKGROUND OF THE INVENTION

As is well known in the aerospace industry art, an increasing number of articles of manufacture are made of composite materials, such as propeller blades for modern aircraft and radomes that house radar emitting devices. Manufacture of such articles requires great care to ensure proper performance. Typically, non-destructive testing of the articles is undertaken by means of immersion ultrasonic inspection.

For example, a composite propeller blade may include an exterior airfoil surface shell bonded to an interior composite laminate spar. It is critical that the bond interface between the shell and spar laminate has no flaws, and that the thickness of the propeller blade assembly conforms to design specifications after the bonding process. Neither characteristic can be visually determined, so immersion ultrasound inspection affords a determination of both the quality of the bond and the consistency of the propeller blade thickness.

Known immersion ultrasound test equipment typically involves a test tank that includes a mounting fixture to secure the workpiece to be tested under an ultrasound transmission medium such as water. A bridge assembly supports an ultrasound transducer mount, and enables the mount to traverse both a longitudinal and transverse axis of the secured workpiece surface so that a transducer within the mount can scan the surface. A transducer position controller controls the bridge assembly and ultrasound transducer mount, and standard ultrasound transducer instrumentation controls signals generated by the transducer, and processes, plots and/or stores information received by the transducer.

In performing an inspection of a workpiece, the transducer position controller directs the bridge assembly and transducer mount to commence a scan of the workpiece in a first direction, parallel to its longitudinal axis, starting at a first exterior lateral edge of the workpiece at a base end and proceeding toward a top end of the workpiece. When that scan is completed, the controller directs the bridge assembly and transducer mount to index the transducer in a direction parallel to the transverse axis of the workpiece a specific increment of length, or index distance, away from the first exterior edge of the workpiece. Next the controller directs the bridge assembly and transducer mount to commence a scan in a second direction opposed to the first direction, parallel to the longitudinal axis of the workpiece, starting at the top and going toward the base end of the workpiece. When that scan is complete, the controller again directs an indexing of the transducer in a direction parallel to the transverse axis away from the exterior edge the same index distance, and initiates another scan in the first direction. The inspection process is repeated until the controller has indexed the transducer entirely across the workpiece to a second exterior edge of the workpiece, opposed to the first exterior edge. During the inspection, the transducer instrumentation processes signals received from the transducer to measure the thickness of the workpiece, or a specific portion thereof, and to detect any internal flaws in the workpiece, in a manner well known in the art.

During ultrasound longitudinal wave testing, virtually all known immersion ultrasonic transducers must be at ninety degrees to the workpiece surface with respect to both its longitudinal and transverse axes and the transducers must remain at a constant distance to the workpiece surface, which conditions are otherwise referred to herein as keeping the transducer normal to the workpiece surface. In the circumstances described above, and as is common with most composite materials needing immersion ultrasonic inspection, the workpiece surface is non-planar, and typically involves differing contours for each different workpiece, such as an elongate, curvilinear propeller blade or a cone-shaped radome. Therefore, the transducer mount must somehow enable the transducer to remain normal to the workpiece surface as the workpiece is inspected.

Many approaches to this requirement have been made, such as that described in U.S. Pat. No. 3,575,043 to Allen, which patent is incorporated herein by reference. In Allen, and in many subsequent commercial applications, the transducer is maintained normal to the surface through an articulating control mechanism that affords movement of the transducer in its three axes of potential movement (for purposes of convenience referred to herein as the longitudinal, transverse, and vertical axes). The articulating control mechanism positions the transducer in response to information loaded into the mechanism that defines the surface of the workpiece. Initially, as in Allen, such information was integrated with the control mechanism through a tape-programming assembly. More modern mechanically encoded systems utilize condensed information transfer methods, yet these systems involve enormous labor costs, as a transducer positioning means must typically be manually re-set in at least one of the three axes after each scan, or at frequent intervals during the inspection, as well as between different workpieces.

More recently, workpiece surfaces have been defined digitally, so that computerized controllers can decrease overall operating times by affording transducer positioning normal to the workpiece surface throughout the entire inspection without the need for manual re-positioning during the inspection. Typical of these computerized immersion ultrasound inspection systems is the "Multiscan Precision Scanning System", Model No. PASAD-MS-1660-03, manufactured by Panametrics, Inc., of Waltham MA 02154. These systems still require specific information defining the surface of each workpiece, so that the system must be re-configured for every different workpiece. Such systems require a digital definition of the workpiece surface mandating substantial investment of time and money prior to an inspection, especially where the workpiece is an older structure that may have been designed before the advent of "Computer Assisted Design", or CAD systems; or where the workpiece is damaged, so that its surface no longer conforms to its designed contours. Additionally, because of the many complexities of the computer-based transducer position controlling means, such systems are very costly compared to the aforesaid manually encoded mechanical test systems.

Accordingly it is the general object of the present invention to provide a mechanical contour follower for positioning an ultrasound transducer that overcomes the problems of the prior art.

It is a more specific object to provide a mechanical contour follower that positions a transducer normal to a workpiece surface throughout an immersion ultrasound inspection that does not require mechanical or computerized re-positioning during the inspection.

It is another specific object to provide a mechanical contour follower that positions a transducer normal to a first workpiece surface and to a second workpiece surface that does not require mechanical or computerized re-positioning between immersion ultrasound testing of the first and second workpieces.

It is yet another object to provide a mechanical contour follower for transducers that overcomes the financial and labor cost problems of transducer positioning means in known immersion ultrasound systems.

The above and other advantages of this invention will become more readily apparent when the following description is read in conjunction with the accompanying drawings.

DISCLOSURE OF THE INVENTION

A mechanical contour follower is disclosed for maintaining a transducer ninety degrees to a workpiece surface, with respect to longitudinal and transverse axes of the workpiece surface, and for keeping the transducer at a constant distance from the workpiece surface during an ultrasound inspection of the workpiece (which conditions are herein referred to as keeping the transducer normal to the workpiece surface). In a particular embodiment, the mechanical contour follower comprises a plunger post slideably secured to a bridge assembly of an ultrasound inspection apparatus; a support frame affixed to the plunger post, having opposed first and second pivot arms; a gimballed mounting means, having an outer ring pivotally secured to opposed pivot ends of the first and second pivot arms, and having an inner disk pivotally secured within the outer ring to produce a gimbal effect; a transducer barrel affixed to a support surface of the inner disk; and a tracking surface of the inner disk opposed to the support surface of the inner disk.

In use of the mechanical contour follower to perform an ultrasound inspection of a workpiece, an ultrasound transducer is secured within the transducer barrel and electrically connected to appropriate ultrasound transducer instrumentation means. The plunger post is slideably secured within a bridge assembly over an ultrasound transmission medium tank of an immersion ultrasound inspection apparatus. The follower is lowered onto a workpiece secured within the tank so that its tracking surface contacts a surface of the workpiece. A transducer position controller means directs the bridge assembly to move the mechanical contour follower in a series of scans in a direction parallel to the longitudinal axis of the workpiece surface, wherein, between each scan, the bridge assembly indexes the follower a specific index distance in a direction parallel to the transverse axis of the workpiece surface, until the entire workpiece surface has been scanned. As the mechanical contour follower moves along a contoured surface of the workpiece, the gimbal effect of the gimballed transducer mount keeps the transducer at ninety degrees to the workpiece surface with respect to the longitudinal and transverse axes of the workpiece surface, and the slidable plunger post enables the transducer secured within the support frame to float in the vertical axis, and thereby remain a constant distance from the workpiece surface, because the tracking surface remains in contact with the workpiece surface in response to gravity, so that the transducer automatically remains normal to the workpiece surface throughout the inspection.

BEST MODE FOR CARRYING OUT THE INVENTION

Referring to the drawings in detail, a mechanical contour follower of the present invention is best shown in FIGS. 1–6, and is generally designated by the reference numeral 10. As best seen in FIGS. 1–6, the mechanical contour follower 10 includes a plunger post 12; a support frame 14 affixed to the plunger post 12, supporting a first pivot arm 16 and an opposed second pivot arm 18; a gimballed mounting means 20, having an outer ring 22 pivotally secured to a pivot end 24 of first pivot arm 16 and an opposed pivot end 26 of second pivot arm 18, and having an inner disk 28 pivotally secured within the outer ring 22 for producing a gimbal effect; a transducer barrel 30 affixed to a support surface 32 of the inner disk 28 for housing a sensor or sensor means for performing inspections such as ultrasound transducer 34; and a tracking surface 36 (best seen in FIGS. 4 and 5) of the inner disk 28 that is opposed to the inner disk's support surface 32, for contacting a workpiece surface 38 (seen in FIGS. 7 and 8).

Figure 7:
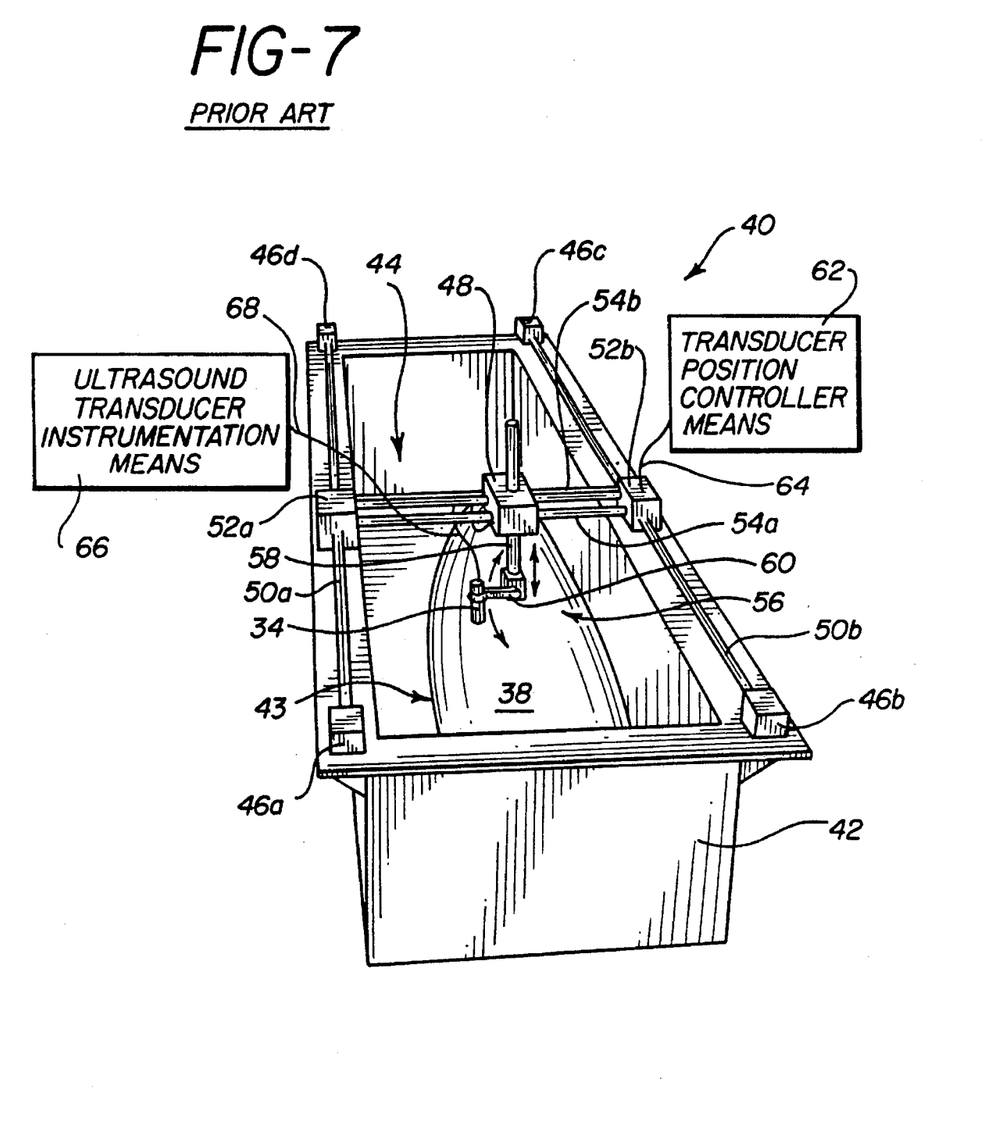
FIG. 7 is a perspective view of a prior art immersion ultrasound testing apparatus.

FIG. 7 shows a prior art immersion ultrasound test apparatus 40 and thereby demonstrates a working environment of the mechanical contour follower 10. The apparatus 40 includes a tank 42 for holding an ultrasound transmission medium such as water (not shown), and for securing a workpiece 43 within the medium; a bridge assembly 44 that straddles the tank 42 and includes longitudinal movement control means 46a, 46b, 46c and 46d for longitudinal positioning of a transducer mount block 48 supported by the assembly 44 along a longitudinal axis (not shown) of the workpiece surface 38 by, for example, rotation of longitudinal rods 50a and 50b, and the bridge assembly 44 also includes a transverse movement control means 52a and 52b for transverse positioning of the ultrasound transducer mount block 48 along a transverse axis of the workpiece surface 38 by, for example, rotation of transverse rods 54a and 54b; and a transducer mount 56 secured to the transducer mount block 48. The transducer mount 56 includes a vertically adjustable securing post 58 and a transducer support arm 60 pivotally and rotationally affixed to the securing post 58. Pivoting and rotating the support arm will enable adjustment of a transducer 34 affixed to the support arm to remain at ninety degrees to both the longitudinal and transverse axes of the workpiece surface 38, while simultaneous vertical adjustment of the securing post 58 will enable the transducer 34 to remain at a constant distance from the workpiece surface 38 as the bridge assembly 44 moves the transducer mount block 48.

In use of the prior art immersion ultrasound test apparatus 40, movement of the bridge assembly is controlled by a transducer position controller means 62 (shown schematically in FIG. 7) well known in the art for positioning a transducer, such as the transducer positioning means used in an "Ultrasonic Inspection System", Model No. JD 85778, manufactured by J. B. Engineering, of Stamford, Conn. 06902. The transducer position controller means 62 communicates with the bridge assembly 44 through prior controller lead 64. Similarly, during use of the prior art immersion ultrasound test apparatus 40, the transducer 34 is controlled by an ultrasound transducer instrumentation means 66 (shown schematically in FIG. 7) well known in the art for controlling signals produced by the transducer and for processing, plotting and/or storing information received by the transducer, such as the transducer instrumentation means used in the "Reflectoscope", Model No QC2000, manufactured by Staveley Instruments, Inc. of Kennewick, Wash., 99336. The ultrasound transducer instrumentation means 66 communicates with the transducer through instrumentation lead 68.

In using the prior art immersion ultrasound test apparatus 40 to inspect the workpiece surface 38, as the transducer position controller means 62 moves the transducer over the contoured surface of the workpiece surface, it is necessary for the controller to adjust the securing post 58 and transducer support arm 60 to maintain the transducer in a position that is ninety degrees to the workpiece surface 38, with respect to longitudinal and transverse axes of the workpiece surface, and for keeping the transducer at a constant distance from the workpiece surface 38 (which conditions are herein referred to as keeping the transducer normal to a workpiece surface). Keeping the transducer normal to the workpiece surface in use of the prior art immersion ultrasound test apparatus therefore requires that the transducer position controller means 62 possess information defining contours of the workpiece surface 38 so that it can make appropriate adjustments to the securing post 56 and transducer support arm 60 as the bridge assembly 44 moves the transducer through an inspection of the workpiece 43.

The mechanical contour follower 10 of the present invention automatically maintains the transducer 34 normal to the workpiece surface, and thereby eliminates the costly and time consuming requirement that the transducer position controller means possess information defining contours of the workpiece surface 38. The mechanical contour follower 10 achieves that automatic maintenance of the transducer normal to the workpiece surface primarily through the gimbal effect of the gimballed mounting means 20.

Figure 1:
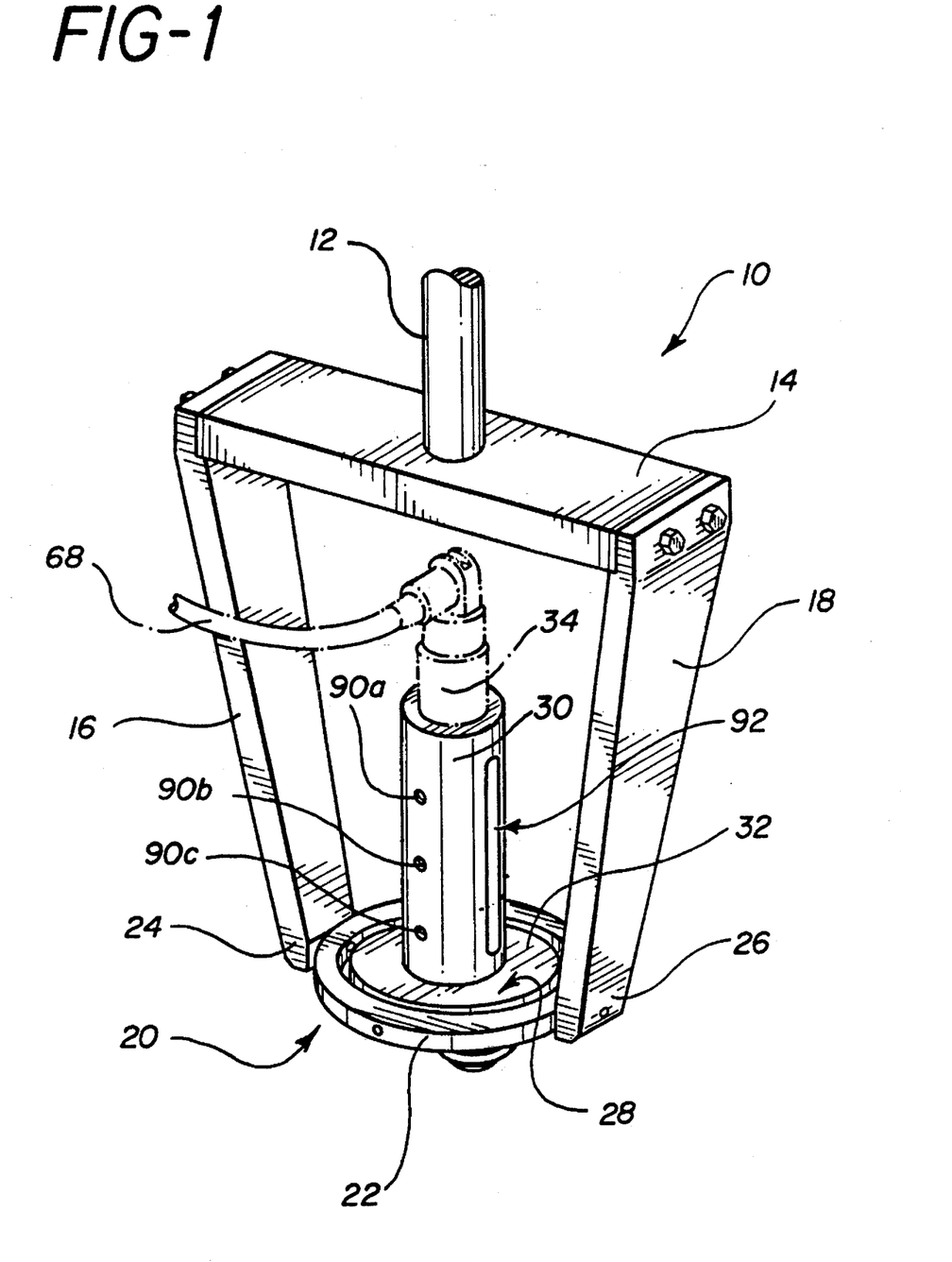
FIG. 1 is a perspective view of a mechanical contour follower constructed in accordance with the present invention, wherein the follower is housing an ultrasound transducer.
Figure 2:
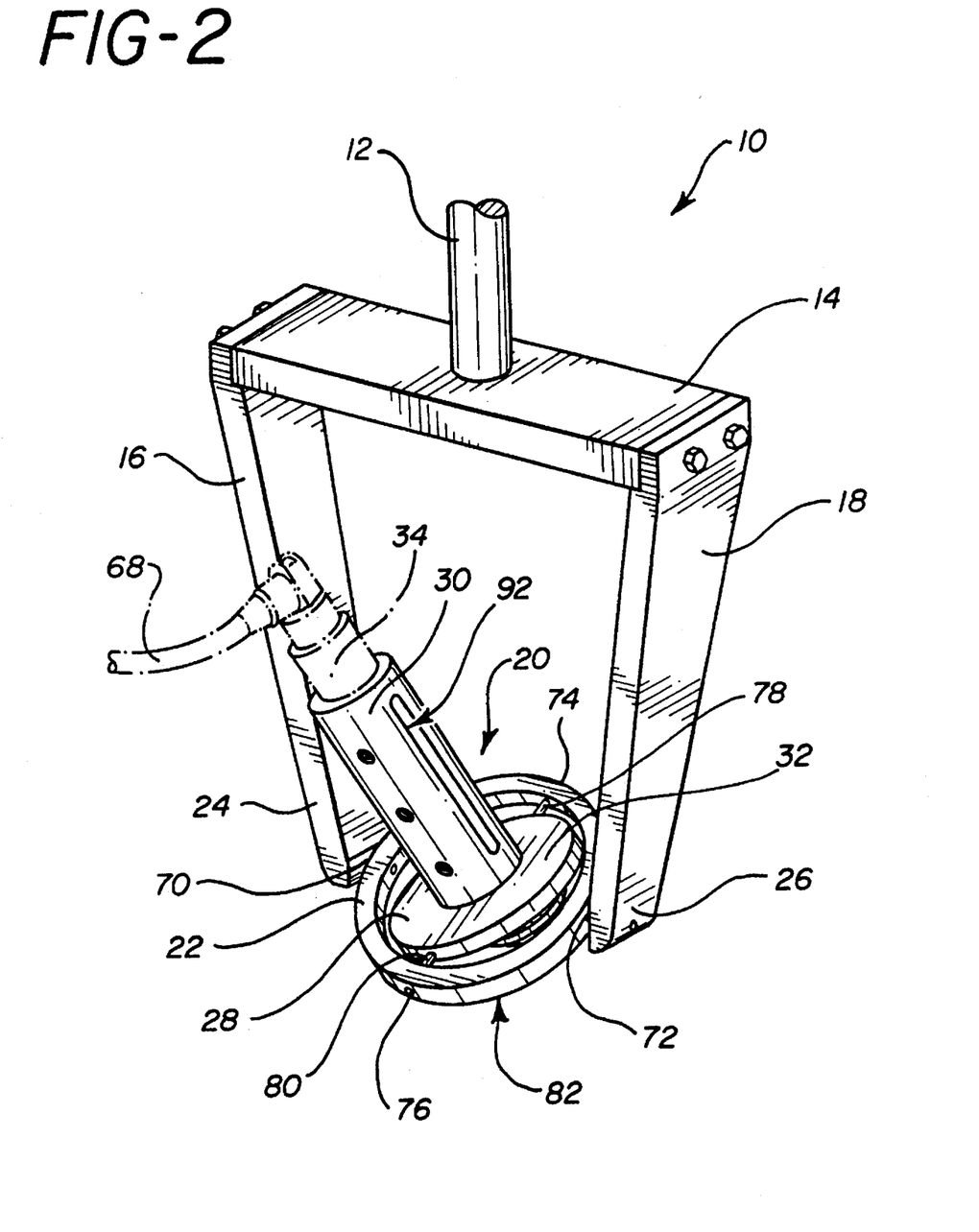
FIG. 2 is similar to FIG. 1, but showing a gimbal effect of the mechanical contour follower's gimballed transducer housing.

As best seen in FIG. 2, the gimbal effect is a result first of the outer ring 22 being secured to the opposed pivot ends 24, 26 of the opposed first and second pivot arms 16, 18 by a first pivot pin 70 that pivotally secures the outer ring 22 to the pivot end 24 of first pivot arm 16 at a point on the outer ring 22 that is one hundred eighty degrees from a point on outer ring 22 where a second pivot pin 72 pivotally secures the outer ring to the pivot end 26 of the second pivot arm 18, so that the outer ring 22 can pivot about an axis defined by first and second pivot pins 70, 72. And the gimbal effect is a result second of the inner disk 28 being secured within the outer ring at first ring pivot point 74 and at a second ring pivot point 76, the first and second ring pivot points being at points on the outer ring 22 that are one hundred eighty degrees from each other, and also being at points on the outer ring 22 that are ninety degrees from the first and second pivot pins, as seen in FIG. 2. The inner disk 28 is pivotally secured to the outer ring 22 by third pivot pin 78, secured to the outer ring 22 at the first ring pivot point 74, and by fourth pivot pin 80, secured to the outer ring 22 at the second ring pivot point 76, so that the inner disk 28 can pivot about an axis defined by third and fourth pivot pins 78, 80. The simultaneous pivoting of the outer ring 22 and inner disk 28 in response to contact between the tracking surface 36 of the mechanical contour follower 10 and the workpiece surface 38 as the follower moves along a nonplanar aspect of the surface 38 is the gimbal effect.

Figure 4:
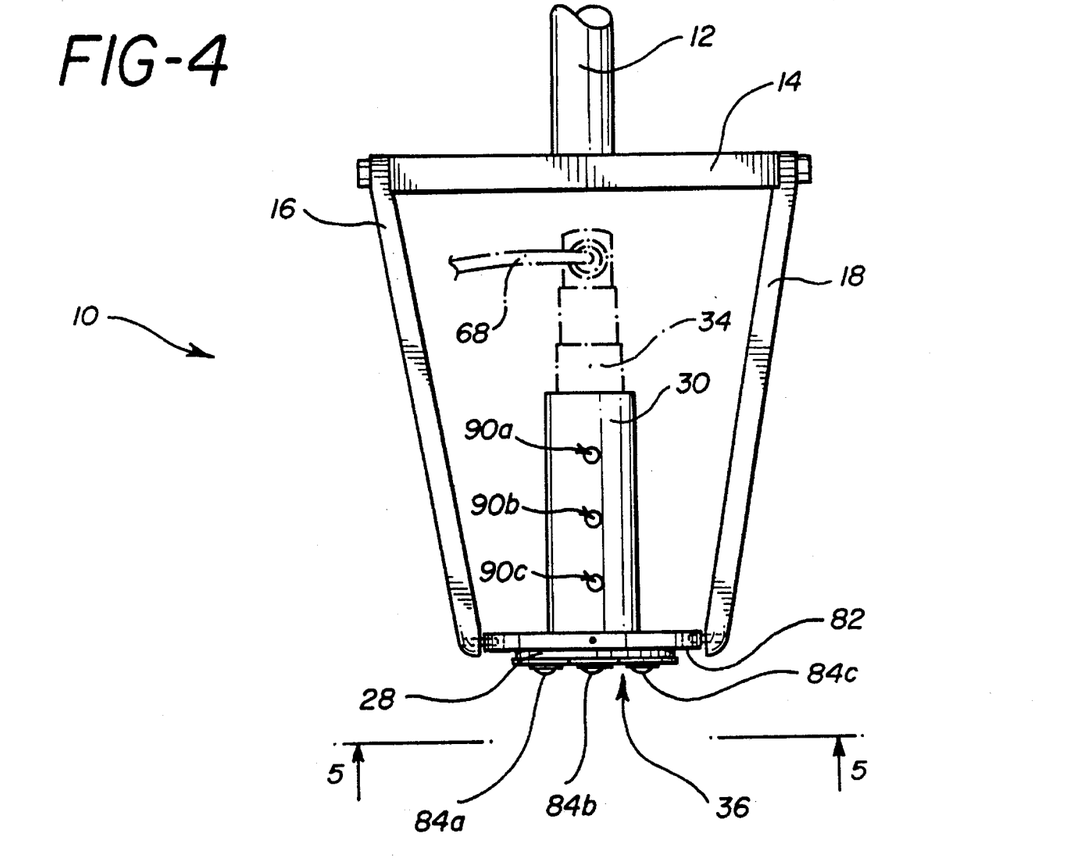
FIG. 4 is side plan view of the FIG. 1 mechanical contour follower.
Figure 5:
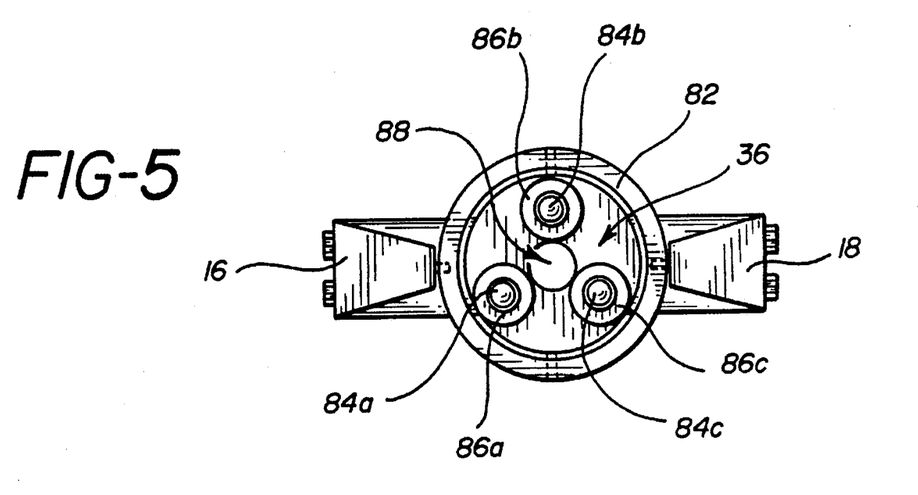
FIG. 5 is a bottom plan view of the FIG. 1 mechanical contour follower.

As best seen in FIGS. 4 and 5, the tracking surface 36 of the mechanical follower 10 is a surface of the inner disk 28 opposed to the support surface 32 of the disk housing the transducer barrel 30. The tracking surface 36 defines a plane that is further from the transducer barrel than a plane defined by a bottom surface 82 of the outer ring 22, the bottom surface 82 being the surface of the outer ring that faces the workpiece surface 38 during operation of the follower 10. The tracking surface 36 may be flat (not shown), or may include a plurality of ball transfer bearings 84a, 84b and 84c secured to the inner disk 28 within bearing housings 86a, 86b, and 86c, as best seen in FIG. 5. The inner disk 28 also defines a transmission throughbore 88 (seen in FIG. 5 only) that permits sound waves from a transducer in the transducer barrel 30 to pass through the tracking surface 36 and out of the mechanical contour 10 follower unimpeded.

Figure 3:
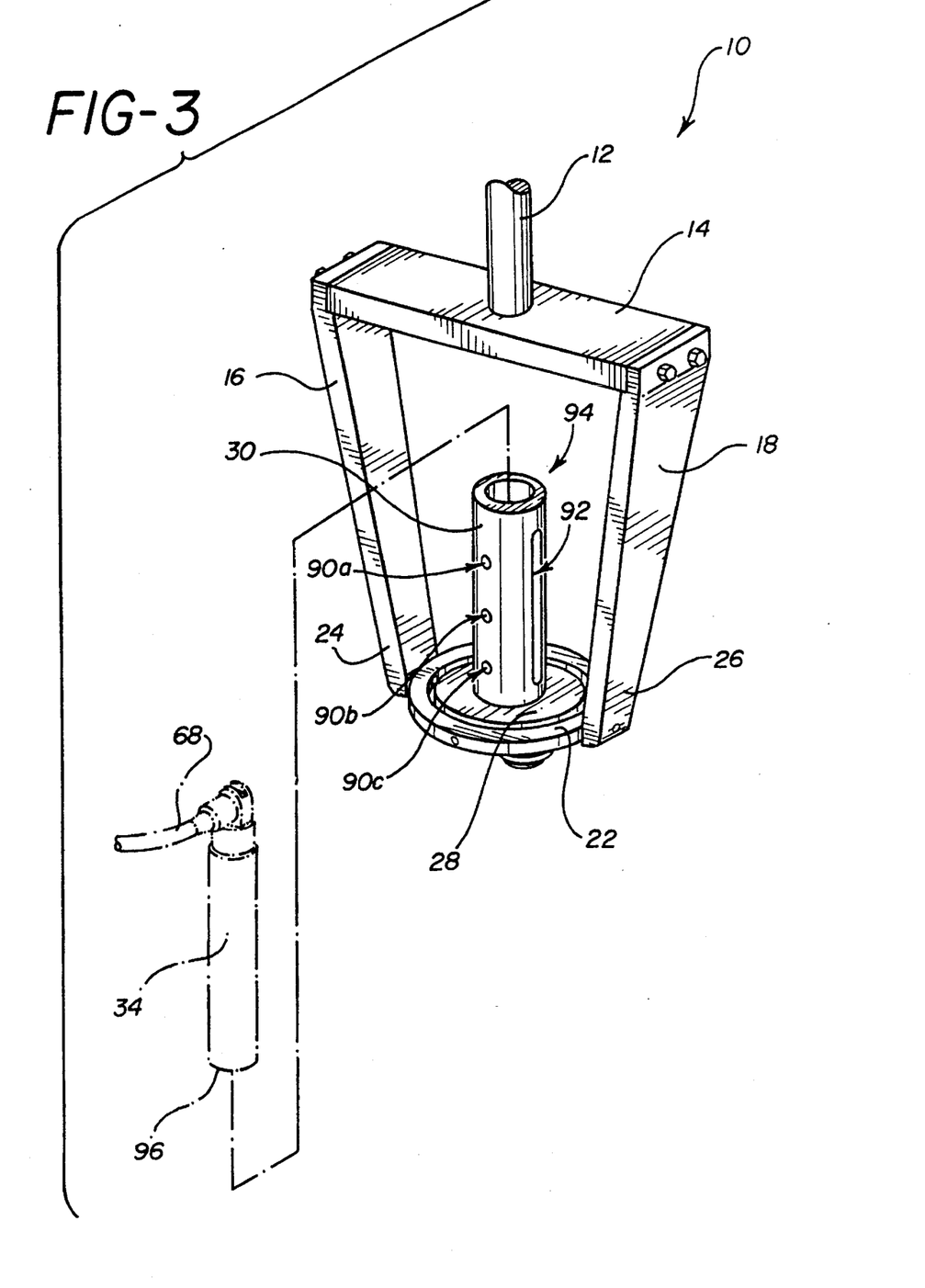
FIG. 3 is similar to FIG. 1, but showing the ultrasound transducer displaced from the mechanical contour follower.

As seen in FIG. 3, the transducer 34 may be readily removed from the transducer barrel 30 and replaced with another transducer by removal of standard set screws (not shown) in set screw holes 90a, 90b, and 90c. Additionally, the transducer barrel 30 defines a measurement slot 92 to assist in positioning a transducer a correct distance from the workpiece surface 38. Moreover, the transducer barrel 30 having a plurality of set screw holes 90a, 90b, 90c, and defining the measurement slot 92 comprises a transducer alignment means 94 for aligning and securing a transducer in the barrel 30 within an infinite variety of specific distances from the workpiece surface 38. For example, if a transducer is to actually contact the workpiece surface 38, the transducer may be passed through the transmission throughbore to rest on the surface. Or, if a transducer is to be set several inches away from the surface 38, that distance is simply marked on the measurement slot, and the transducer transmission head 96 is positioned at the marked distance, and secured by one or more set screws in the set screw holes 90a, 90b, 90c. Practically, the transducer alignment means is very valuable. It is common to inspect a workpiece surface, and then to inspect a component within the workpiece, such as a propeller blade spar. The transducer alignment means affords re-alignment of the same transducer within the transducer barrel to achieve inspection of the spar, without having to change to a transducer having a different focal length.

Figure 8:
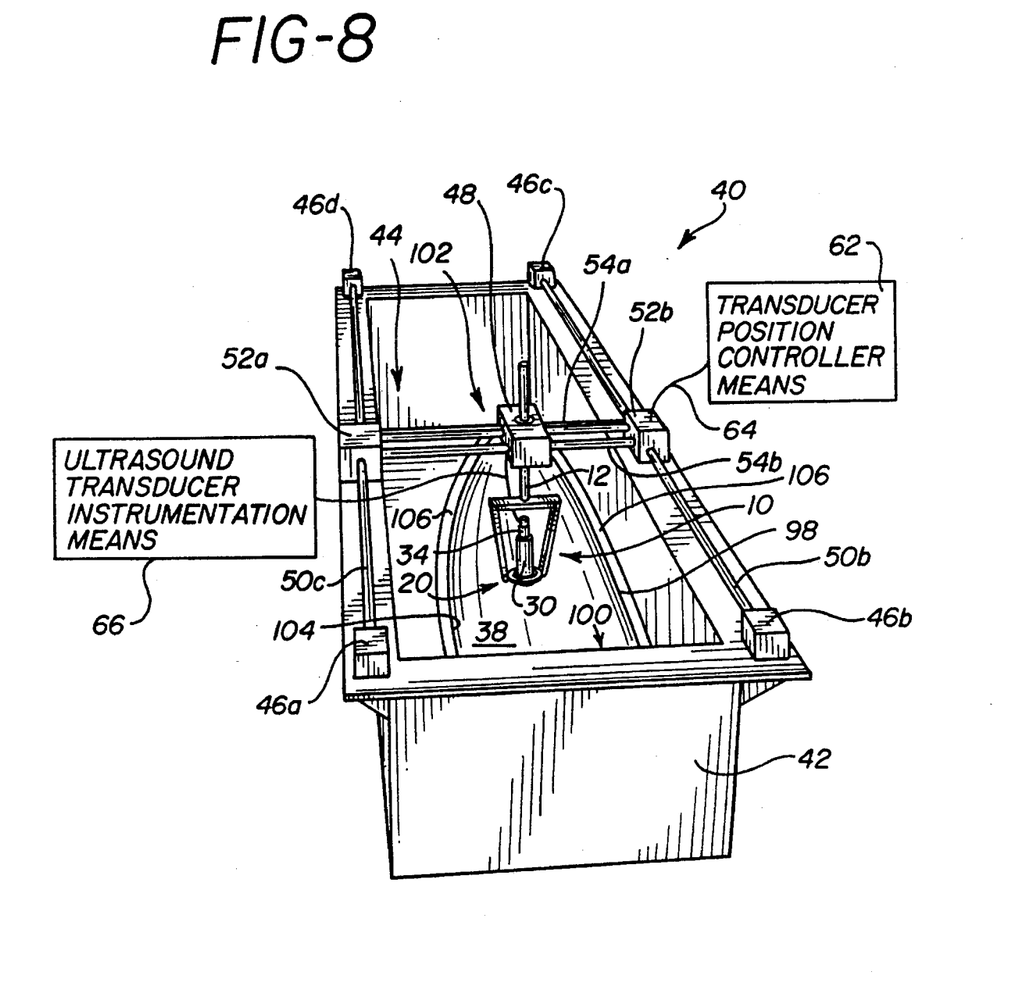
FIG. 8 is perspective view of an immersion ultrasound testing apparatus utilizing a mechanical contour follower of the present invention.

In use of the mechanical contour follower 10 of the present invention, as best shown in FIG. 8, the transducer mount 56 of the prior art immersion ultrasound test apparatus 40 is simply replaced by the mechanical contour follower 10 so that the transducer mount block 48 slideably engages the plunger post 12 of the follower 10, and the tracking surface 36 of the inner disk 28 rests upon the surface 38 of the workpiece 43. To perform an inspection of the surface 38, the transducer position controller means 62 directs the bridge assembly 44 to position the mechanical contour follower 10 to commence a scan of the workpiece surface 38 in a first direction, parallel to a longitudinal axis of the surface 38, starting at a first exterior edge 98 of the workpiece surface at a base end 100 and proceeding toward a top end 102 of the surface 38. When that scan is completed, the controller means 62 directs the bridge assembly 44 to index the follower 10 in a direction parallel to a transverse axis of the workpiece surface a specific increment of length, or index distance, away from the first exterior edge 98 of the workpiece. Next the controller means directs the bridge assembly 44 and follower 10 to commence a scan in a second direction opposed to the first direction, parallel to the longitudinal axis of the workpiece surface 38, starting at the top end 102 and going toward the base end 100 of the surface. When that scan is complete, the controller means again directs an indexing of the mechanical contour follower 10 in a direction parallel to the transverse axis away from the first exterior edge 98 the same index distance, and initiates another scan in the first direction. That scanning and indexing process is repeated until the controller means 62 has indexed the transducer entirely across the workpiece surface 38 to a second exterior edge 104 of the workpiece surface, opposed to the first exterior edge 98. During the inspection, the transducer instrumentation means 66 processes signals received from the transducer 34 to measure the thickness of the workpiece surface 38, or a specific portion thereof, and to detect any internal flaws in the workpiece 43, in a manner well known in the art.

Figure 6A:
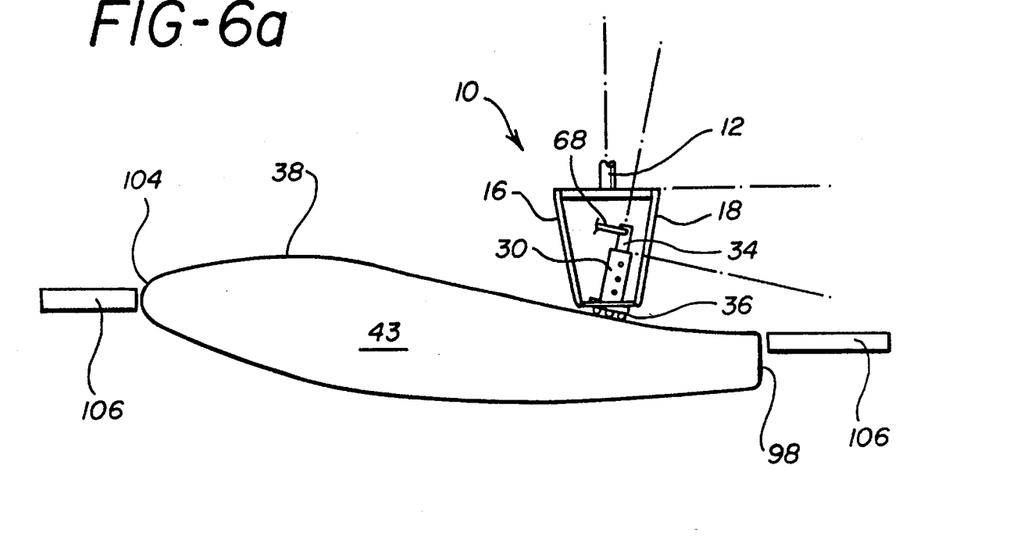
FIGS. 6a and 6b are partial fragmentary views of the FIG. 1 mechanical contour follower, showing the follower deployed in different positions along a contoured surface of a workpiece.
Figure 6B:
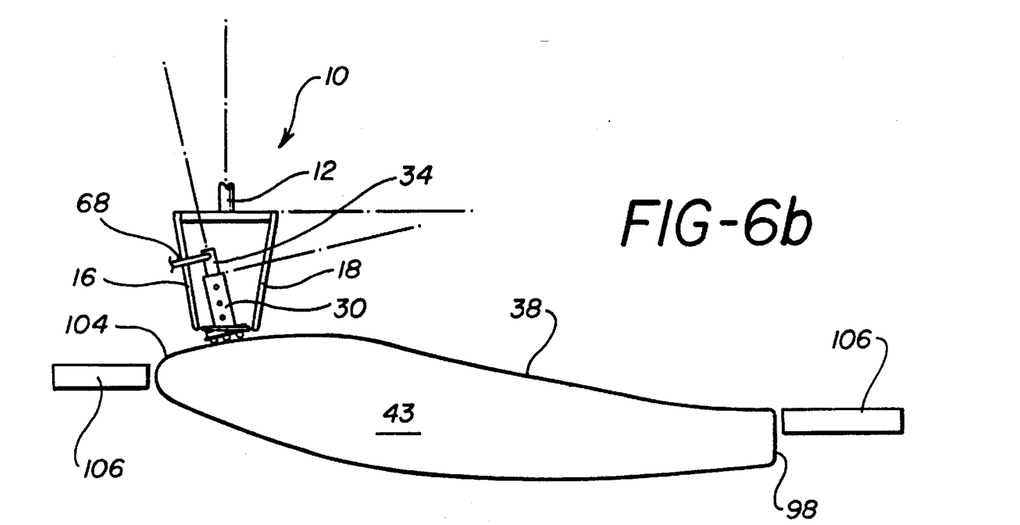

In circumstances wherein the tracking surface 36 of the inner disk 28 is not flat but includes protrusions such as the ball transfer bearings, a support mold 106, as seen in FIGS. 6a, 6b and 8, surrounds the workpiece 43 so that the mold 106 offers support to the mechanical contour follower as the transducer throughbore 88 is over an exterior edge 98, or 104 of the workpiece surface.

As best seen in FIGS. 6a and 6b, as the mechanical contour follower 10 is moved to different positions (e.g., FIG. 6a or FIG. 6b) on the surface 38 of the workpiece 43, the gimballed mounting means 20 combined with the floating of the plunger post 12 in response to gravity enables the transducer 34 to remain normal to the workpiece surface. Because the mechanical contour follower 10 automatically remains normal to any workpiece surface, there is no need for the transducer position controller means 62 to first possess information defining the surface of the workpiece. Additionally, the transducer alignment means 94 allows simple re-alignment of one transducer in the transducer barrel 30 to enable inspections of differing depths of one workpiece, or to enable inspection of differing workpieces by one transducer. Consequently, the mechanical contour follower 10 of the present invention decreases costs and labor requirements for immersion ultrasound inspections of workpieces by both minimizing the information retention and mechanical control requirements of a transducer position controller means, and also by enabling a smaller variety of transducers to perform multiple inspections on multiple workpieces.

While the present invention has been described and illustrated with respect to a particular construction of a mechanical contour follower, it will be understood by those skilled in the art that the present invention is not limited to this particular example. For, example, the follower could be readily employed in non-immersion based inspection apparatus, with different sensing devices than ultrasound transducers. Accordingly, reference should be made primarily to the attached claims rather than to the foregoing specification to determine the scope of the invention.

What is claimed is:

1. A mechanical contour follower for maintaining a sensor at ninety degrees to a surface of a workpiece with respect to longitudinal and transverse axes of the surface and for maintaining the sensor at a constant distance from the surface of the workpiece being inspected by the sensor, comprising:

a. a plunger post slideably affixed to a test apparatus;

b. a support frame affixed to the plunger post; and c. a gimballed mounting means mounting the sensor and pivotally affixed to opposed first and second pivot arms of the support frame for producing a gimbal effect on the sensor as the mechanical contour follower contacts and moves along the workpiece surface while the sensor inspects the workpiece wherein the gimballed mounting means includes a transducer alignment means for aligning and securing the sensor in a barrel of the gimballed mounting means within a plurality of specific distances from the workpiece surface.

2. A mechanical contour follower for maintaining a sensor at ninety degrees to a surface of a workpiece with respect to longitudinal and transverse axes of the surface and for maintaining the sensor at a constant distance from the surface of the workpiece being inspected by the sensor, comprising:

a. a plunger post slideably affixed to a test apparatus;

b. a support frame affixed to the plunger post; and c. a gimballed mounting means mounting the sensor and pivotally affixed to opposed first and second pivot arms of the support frame for producing a gimbal effect on the sensor as the mechanical contour follower contacts and moves along the workpiece surface while the sensor inspects the workpiece, the gimballed mounting means comprising i. an outer ring pivotally secured by first and second pivot pins to opposed first and second pivot ends of the first and second pivot arms so that the first pivot pin is secured to a point on the outer ring that is one hundred eighty degrees from a point on the outer ring to which the second pivot pin is secured;

ii. an inner disk pivotally secured within the outer ring by third and fourth pivot pins so that the third pivot pin is secured to a point on the outer ring that is one hundred eighty degrees from a point on the outer ring to which the fourth pivot pin is secured and the third and fourth pivot pins are at points on the outer ring that are ninety degrees from the points on the outer ring to which the first and second pivot pins are secured, so that the outer ring pivots about an axis that is defined by the first and second pivot pins and the inner disk pivots about an axis defined by the third and fourth pivot pins;

c. a support surface of the inner disk that supports the sensor;

d. a tracking surface of the inner disk opposed to the support surface, wherein the tracking surface contacts the workpiece surface during an inspection, the tracking surface defining a plane that is closer to the workpiece surface than a plane defined by a bottom surface of the outer ring.

3. An improved inspection apparatus for non-destructive testing of articles of manufacture having a tank for holding an ultrasound medium around a workpiece, and a bridge assembly that adjustably straddles the tank and supports a transducer mount block, the improvement comprising a mechanical contour follower for maintaining an ultrasound transducer normal to a surface of the workpiece being inspected by the transducer, and the apparatus including a support mold surrounding an exterior edge of the workpiece so that the support mold supports the mechanical contour follower as the mechanical contour follower inspects the exterior edge, the mechanical contour follower including a plunger post slideably affixed to the transducer mount block, a support frame affixed to the plunger post, and a gimballed mounting means mounting the transducer and pivotally affixed to opposed first and second pivot arms of the support frame for producing a gimbal effect on the transducer as the mechanical contour follower contacts and moves along the workpiece surface while the transducer inspects the workpiece.

4. A mechanical contour follower for maintaining an ultrasound transducer normal to a surface of a workpiece being inspected by the ultrasound transducer, comprising:

a. a plunger post slideably affixed to an immersion ultrasound test apparatus including a tank for holding an ultrasound transmission medium around the workpiece, and a bridge assembly that straddles the tank and supports a transducer mount block that slideably engages the plunger post of the mechanical contour follower so that the bridge assembly positions the transducer mount block to scan the workpiece during an inspection, the test apparatus having a transducer position controller means for controlling movement of the bridge assembly and the transducer mount block of the bridge assembly, and the test apparatus having a transducer instrumentation means for controlling signals produced by the transducer and for processing information received by the transducer;

b. a support frame affixed to the plunger post; and c. gimballed mounting means mounting the ultrasound transducer and pivotally affixed to opposed first and second pivot arms of the support frame for producing a gimbal effect on the ultrasound transducer as the mechanical contour follower contacts and moves along the workpiece surface while the ultrasound transducer inspects the workpiece, the gimballed mounting means including a transducer alignment means for aligning and securing the transducer in a barrel of the gimballed mounting means within a plurality of specific distances from the workpiece surface.

5. The mechanical contour follower of claim 4, wherein the gimballed mounting means comprises:

a. an outer ring pivotally secured by first and second pivot pins to opposed first and second pivot ends of the first and second pivot arms so that the first pivot pin is secured to a point on the outer ring that is one hundred eighty degrees from a point on the outer ring to which the second pivot pin is secured;

b. an inner disk pivotally secured within the outer ring by third and fourth pivot pins so that the third pivot pin is secured to a point on the outer ring that is one hundred eighty degrees from a point on the outer ring to which the fourth pivot pin is secured and the third and fourth pivot pins are at points on the outer ring that are ninety degrees from the points on the outer ring to which the first and second pivot pins are secured, so that the outer ring pivots about an axis that is defined by the first and second pivot pins and the inner disk pivots about an axis defined by the third and fourth pivot pins;

c. a support surface of the inner disk that supports the transducer barrel;

d. a tracking surface of the inner disk opposed to the support surface, wherein the tracking surface contacts the workpiece surface during an inspection, the tracking surface defining a plane that is closer to the workpiece surface than a plane defined by a bottom surface of the outer ring.

6. The mechanical contour follower of claim 5, wherein the test apparatus includes a support mold surrounding an exterior edge of the workpiece so that the support mold supports the mechanical contour follower as the mechanical contour follower inspects the exterior edge.

\* \* \* \* \*